US006106847A

United States Patent [19]

Ferrero et al.

[11] Patent Number: 6,106,847

[45] Date of Patent: Aug. 22, 2000

[54] STABLE MULTIPLE PHASE EMULSION OF THE TYPE $O_1/W/O_2$

[75] Inventors: Louis Ferrero, Nice, France; Karin Golz; Leonhard Zastrow, both of Monaco, Monaco; Klaus Stanzl, White Plains, N.Y.

[73] Assignee: Lancaster Group GmbH, Ludwigshafen, Germany

[21] Appl. No.: 08/924,241

[22] Filed: Sep. 5, 1997

[30] Foreign Application Priority Data

Sep. 13, 1996 [DE] Germany ........................... 196 38 729

[51] Int. Cl.[7] ....................................................... A61K 7/48

[52] U.S. Cl. .............................. 424/401; 424/59; 424/69; 514/937; 514/938

[58] Field of Search ..................... 424/401, 59; 514/937, 514/938, 69

[56] References Cited

U.S. PATENT DOCUMENTS 5,391,321 2/1995 Grüning et al. .

FOREIGN PATENT DOCUMENTS

| | | |
|---|---|---|
| 218394 | 9/1986 | European Pat. Off. . |
| 322501 | 2/1989 | European Pat. Off. . |
| 391124 | 3/1990 | European Pat. Off. . |
| 425958 | 10/1990 | European Pat. Off. . |
| 648102 | 6/1993 | European Pat. Off. . |
| 614656 | 1/1994 | European Pat. Off. . |
| 692237 | 5/1995 | European Pat. Off. . |
| 7101844A | 9/1993 | Japan . |
| 7101849A | 9/1993 | Japan . |
| WO 96/02223 | 2/1996 | WIPO . |

OTHER PUBLICATIONS

Ross, S. and Morrison, I., “Colloidal Systems and Interfaces”, John Wiley & Sons, New York, p. 17–19.

Couarraze, G. and Grossiord, J.L. “Initiation a la Rheology”.

*Primary Examiner*—Jyothsan Venkat

*Attorney, Agent, or Firm*—Collard & Roe, P.C.

[57] ABSTRACT

The invention relates to a stable multiple phase emulsion of the $O_1/W/O_2$ type with high proportions of the primary $O_1/W$ emulsion. The new emulsions have an emulsifier-free primary oil-in-water phase consisting of a viscoplastic aqueous gel containing the finely distributed inner oil droplets together with a gelling agent, wherein the thixotropic primary oil-in-water phase has a yield point in the range from 20 to 100 Pa and a plastic viscosity of 0.01 to 0.1 Pa·s and contains at least one lipophilic agent in the primary oil; and a secondary oil phase in which the primary oil-in-water phase is present together with a lipophilic emulsifier; and wherein the proportion of the inner oily phase is from 10 to 35 % by weight relative to the total weight of the emulsion. The higher proportions of the inner oily phase render possible higher proportions of organic sun protection agents with simultaneous avoidance of skin irritations.

16 Claims, No Drawings

STABLE MULTIPLE PHASE EMULSION OF THE TYPE $O_1/W/O_2$

FIELD OF THE INVENTION

The invention relates to a stable multiple phase emulsion of the $O_1/W/O_2$ type with high proportions of the inner oily phase $O_1$.

BACKGROUND OF THE INVENTION AND PRIOR ART

Various $O_1/W/O_2$ emulsions have already been disclosed (O/W/O=oil-in-water-in-oil) wherein the primary O/W emulsion (O/W=oil-in-water) is to be kept stable with the aid of hydrophilic ionic or non-ionic emulsifiers (see e.g. EP 391124, EP 425958). In EP 218394 only 4.5% of the oil phase is emulsified in the primary emulsion with at least 1.25% of the hydrophilic emulsifier sodium alkyl polyether sulfonate.

From JP-A-07-101849 a multiple phase emulsion of the O/W/O type is known in which kojic acid, 5-hydroxy-2-(hydroxymethyl)1,4-pyrone is contained as an active ingredient. JP-A-07-101844 describes an O/W/O emulsion containing two different UV-filters and showing a reduced skin irritation.

Problematic with the well-known emulsions of this type is that particularly for sun protection preparations with higher sun protection factors large amounts of lipophilic UV-absorbent must be introduced into the inner oil phase and that this has hitherto only been possible by increasing the hydrophilic emulsifier proportion. In this way however, the stability of the overall emulsion and thus also of the outer oil phase is impaired since conventional O/W/O emulsions tend to break down to simple O/W emulsions.

It is furthermore known that increased amounts of oil, particularly of silicone oils, led to difficulties in the production of stable W/O formulations. Poor stability is shown which results in too high a fluidity. The need thus also exists to incorporate more oil in the oily phase of a W/O formulation without loss of stability.

OBJECT OF THE INVENTION

The object of the invention is to develop a new multiple phase emulsion system of the O/W/O type containing high proportions of the inner oil phase.

A further object of the invention is the prevention of skin irritation by UV-absorbents all but completely.

A further object of the invention consists of a production process for O/W/O type emulsions of long-lasting stability.

SUMMARY OF THE INVENTION

According to the invention the stable $O_1/W/O_2$ type multiple phase emulsion consists of a primary oil-in-water phase without emulsifier, in which the inner oil droplets are present in a viscoplastic aqueous gel essentially coalescence-free and finely distributed together with a gelling agent, preferably an amphiphilic polyacrylate block copolymer, wherein the yield point of the viscoplastic gel is in the range from 20 to 100 Pa and their plastic viscosity from 0.01 to 0.1 Pa·s, and wherein the inner oily phase occupies a proportion of 10 to 35% by weight relative to the total emulsion, and the secondary oil contains at least one lipophilic agent; and a secondary oil phase, in which the primary O/W phase exists together with a lipophilic emulsifier.

DETAILED DESCRIPTION OF THE INVENTION

Following Ross, S. and Morrisson, I. "Colloidal Systems and Interfaces", John Wiley & Sons, New York, Page 17–19, the plastic flow can determined in relation to shear stress and shear rate. The rheogramm of a plastic material describes one that does not flow until sufficient stress is applied. The stress at which the flow begins is called YIELD POINT; at stresses larger than the yield point, the rate of flow is approximately linear with the shearing stress. This yield point is also called yield value.

The plastic viscosity is derived from the slope of the graph line in the rheogramm and can be calculated by the yield point as the experimental result (see also Couarraze, G. and Grossiord, J. L. "Initiation a la Rheology", Lavoisier-Tec&Doc, Paris, 2nd edition, p. 75–78) Yield point of plastic bodies which are also named Bingham or Casson bodies are for example for spraying laquer: low yield point of 0–1 Pa (low plastic viscosity of 0.01–0.1 Pa·s), paints od ketchup: medium yield point of 5–50 Pa (low plastic viscosity of 0.1–0.5 Pa·s), ointments: high yield point of 100–1000 Pa (medium to high plastic viscosity of 0.5–5 Pa·s).

According to the invention the stable $O_1/W/O_2$ type multiple phase emulsion consists of a primary oil-in-water phase without emulsifier, in which the inner oil droplets are present in a viscoplastic aqueous gel essentially coalescence-free and finely distributed together with a gelling agent, preferably an amphiphilic polyacrylate block copolymer, wherein the yield point of the viscoplastic gel is in the range from 20 to 100 Pa and their plastic viscosity from 0.01 to 0.1 Pa·s, and wherein the inner oily phase occupies a proportion of 10 to 35% by weight relative to the total emulsion, and the secondary oil contains at least one lipophilic agent; and a secondary oil phase, in which the primary O/W phase exists together with a lipophilic emulsifier.

For elucidation it must be pointed out that the inner oil droplets (inner oily phase) are constantly incorporated in the primary $O_1$/W phase.

In the case of the viscoplastic gel of the invention there were determined for the primary $O_1$/W emulsion a medium to high yield point of 20 to 100 Pa. These values were determined by the known Casson equation. The gel structure is very quickly build up, even after a temporary destruction by a large shear rate. This property is called Thixotropie and is essential for the inventive concept.

Suitable as gelling agents for the primary $O_1$/W phase are all gelling agents bestowing distinct viscoplastic properties on the aqueous phase and possessing sufficient stabilizing and dispersing characteristics to generate correspondingly small droplets incorporated in finely distributed form in the second stage by the secondary oil phase.

Particularly suitable for this are polyacrylate block colymers with alternating hydrophilic and hydrophobic blocks, particularly Hypan® hydrogels of the TN type. These hydrogels form a fine three-dimensional net in the aqueous medium which can be reversible degraded by high shear stresses and/or heat. Suitable hydrogels are (CTFA names): Acrylic acid/Acrylonitrogens copolymer such as Hypan® SA-100H-100H or Hypan® SR-150H-150H; Ammonium acrylates/Acrylonitrogens copolymer such as Hypan® SS-201; Polyquaternium-31 such as Hypan® QT-100 (all produced by Kingston Technology Inc., N. Y., USA).

The amphiphilic polyacrylate block copolymer is responsible herein for both the viscoplastic properties as well as for the good distribution of the inner oil phase in the aqueous gel.

The addition of the Hypan® TN gels takes place in very small amounts ranging from 0.2 to 0.5% by weight relative to the total mass of the emulsion.

As gelling agent a three-layer clay mineral such as smectite can be used. Suitable above all are synthetic smectites with tri-octahedral coordinated cations prepared from magnesium silicates and alkali cations, for example Smectite SWN® (from Nikko Chemicals Corp.). The amounts of smectites used are higher than those used for Hypan hydrogels, that means about 1–3% by weight.

With the aid of the gelling agent a thixotropic aqueous gel containing finely distributed oil droplets is obtained and wherein this primary oil-in-water phase has a yield point in the range from 20 to 100 Pa. The yield point can be increased further by addition of polyethylene glycol, e.g. by addition of Glycereth-26 or a polyethylene glycol such as PEG-8.

Moreover essential to the invention is the very low plastic viscosity from 0.01 to 0.1 Pa·s.

The oil used for the primary oil phase is a normal triglyceride such as vegetable or synthetic oils commonly used in cosmetic formulations. Also included are linear or branched esters of fatty acids and alcohols, esters of fatty acids and glycols such as propylene glycol ester as well as esters of hydroxyfatty acids. Essential for the primary oil is the compatibility with the active agents of the oil phase and the interaction with the polyacrylate block copolymers in order to form a sufficiently thin (low viscosity) primary $O_1$/W emulsion which however has a sufficient yield point.

Esters of fatty acids and alcohols of medium chain length have proved particularly advantageous for sun protection preparations such as $C_{12}$–$C_{13}$ Alkyl Octanoate esters used together with organic sun protection agents. Other special esters can be added such as $C_{12}$–$C_{13}$ Alkyl Malate, $C_{12}$–$C_{13}$Alkyl Lactate and $C_{12}$–$C_{13}$ Alkyl Citrate.

The preferred vegetable oils are avocado oil, rice bran oil, jojoba oil and Babassu oil.

Other esters such as diethylene glycol dioctanoate or diisononanate, propylene glycol dicaprylate, neopentyl glycol diheptanoate etc. can be used.

The primary $O_1$/W-emulsion contains at least one lipophilic agent in the primary oil droplets. This agent is preferably a UV-protection agent or a UV-blocking agent such as Octyl Methoxycinnamate, Octyl Salicylate; Homosalate; Menthyl Anthranilate; Octocrylene; Benzophenone-3; Octyl Dimethyl PABA [p-aminobenzoic acid]; 4-Methylbenzilidene Camphor; Butyl Methoxy-Dibenzoyl methane.

The primary (inner) oil phase and also the secondary (outer) oil phase may moreover contain: liposoluble vitamins such as vitamin A esters (Retinol palmitate, acetate); vitamin E such as Tocopherol acetate or Tocopherol linolate; vitamin $B_2$, vitamin $D_6$; vitamin F;

Anti-inflammatory agents such as Bisabolol, Glycerrethinic acid, Stearyl Glycerrhetinate; polyunsaturated fatty acids or fatty acid esters thereof such as avocado, peanut and borrage oils; jojoba oil and calendula oil etc.; unsaponifiables such as shea butter, avocado, soybean oil etc.; lanolin and lanolin derivatives; emollients such as perhydrosqualene, perfluoropolyethers.

In the aqueous phase certain hydrophilic constituents may be present as humectants such as e.g. glycerol, propylene glycol, different grades of PEG, sorbitol, glucose, maltose etc.; Panthenol or Allantoin; peptides or proteins and their derivatives such as collagen, elastin etc.; water soluble vitamins such as ascorbic acid; preservatives such as chlorohexidine, phenoxyethanol, dimethyl Hydantoin, imidazolidinyl urea.

The secondary or outer oil phase in which the primary oil-in-water emulsion is emulsified as finely distributed droplets is formed by any oil for cosmetic formulations, such as e.g. silicone oil, synthetic fatty acid esters, paraffin oils, waxes such as micro-waxes, beeswax, castor wax or polyethylene wax.

Silicone oil has proved particularly advantageous particularly then if a sun protection preparation is to be produced. Silicone oil is preferred because it does not feel greasy, shows good spreadability on the skin and good water repellence. Linear or cyclic polydimethylsiloxanes such as Cyclomethicone to which further organopolysiloxanes can be added such as Alkyldimethicone, Alkoxydimethicone (Abil® waxes), or Phenyldimethicone or Phenyltrimethicone can be used.

Other suitable polymers such as silicone acrylates and vinyl silicones or fluorosilicones or perfluoro-polyethers (such as Fomblin®) as well as silicone gums such as Dow Corning 1401® and 1403® can be added to the silicone oils to improve the blocking effect and the ability to form films.

Suitable emulsifiers can be used for the secondary oil phase corresponding to the oils employed. If silicone oils form the secondary oil phase then emulsifiers such as polysiloxane-polycetyl-polyethylene glycol copolymers (CTFA-name: Cetyl Dimethicone Copolyol) e.g. Abil® EM90 (Goldschmidt), Abil® WE09 (Goldschmidt), Q2-5200 (Dow Corning) are suitable. To be advantageous the HLB value [hydrophilic-lipophilic balance] of these emulsifiers should not be greater than 8.

Further agents may be contained in the secondary oil phase. Particularly in the case of sun protection preparations sun protection agents may be contained, preferably inorganic mineral pigments such as micronized $TiO_2$ or ZnO. Other powdery products such as Polyamid-12 (Orgasol® from Atochem), polymethyl methacrylate (Covabead® from Wacker) or polymethyl silsesquioxan (Tospearl® from Kobo, Japan) for improvement of the skin feeling may also be present.

A particularly favorable concept for sun protection preparations consists in detaining organic sun protection agents that can produce irritation effects on the skin in the primary oil phase, and in dispersing the skin compatible inorganic pigments in the secondary oil phase. In this way a preparation is obtained which is particularly skin compatible because of the high proportion of primary oil-in-water phase and the possibility of retaining high proportions of organic sun protection agents in the primary oil phase and thus achieving very high sun protection factors, and which is clearly superior to comparable preparations.

Hitherto unnamed agents, additives and auxiliary substances commonly used in cosmetic and dermatological formulations may also be contained in the preparation according to the invention based on a multiple phase emulsion. Restrictions only exist insofar as these constituents should not disturb the structuring of the multiple phase emulsion. Similarly the viscoplastic characteristic of the primary $O_1$/W-emulsion should not be disturbed e.g. by electrolytes which destroy the gel network. Also, the use of hydrophilic emulsifier with HLB values greater than 12 for the outer oil phase would lead to destabilization of the $O_1/W/O_2$ emulsion and is thus inexpedient.

In a preferred embodiment in the inner oily phase a micronized mineral pigment such as ZnO, $TiO_2$, $SiO_2$, $ZrO_2$ is present alone or associated with chemical filters. The main advantages as a sun protecting agent are (1) a very good feeling during skin application caused by the silicone nature of the outer layer phase, (2) a better UV sunscreen efficacy for e.g. $TiO_2$ in an adequate oily phase than organic esters, and the silicone phase is prevented of any interference and (3) attenuation of the whitening effect normally associated with physical UV absorbers when they are dosed at 5% by weight or more in sun products. The range of mineral pigments in a multiple emulsion, e.g. $TiO_2$ (solid)/Oil/Water/Silicone is betweeen 0.5–8% by weight, referred to the total weight of the emulsion.

The invention also relates to a production process for a stable multiple phase emulsion of the $O_1/W/O_2$ type. The process comprises the following steps:

a gelling agent such as a polyacrylate block copolymer is dispersed in an aqueous phase until the formation of a gel;

the aqueous phase and a primary oil phase separated from it are heated to a temperature of maximally 70° C.;

the primary oil phase is dispersed in the aqueous phase by application of intensive shear stresses at the increased temperature;

the primary O/W-emulsion is subsequently cooled under moderate stirring until a gel formation reoccurs;

the primary O/W-emulsion is dispersed in the secondary oil phase at surroundings temperature under moderate stirring.

The invention also relates to the use of a stable multiple phase emulsion of the $O_1/W/O_2$ type as a sun protection preparation or make-up formulation with a primary oil-in-water phase consisting of a viscoplastic gel containing at least one organic UV-absorbant in the oil droplets, and a secondary oil phase of a silicone oil containing one or more inorganic UV-absorbants, wherein the oil proportion in each phase is in the range from 15 to 30% by weight relative to the total weight of the emulsion.

The invention is to be more closely elucidated by examples. All specifications refer to weight if nothing else is indicated.

EXAMPLE 1

Production of the multiple phase emulsion of $O_1/W/O_2$ type

A polyacrylate block copolymer as gelling agent was dispersed in an aqueous phase and a gel formed. The pH value was adjusted to around 6. An oil was heated at the same time to around 70° C. and dispersed in the gel phase which had around the same temperature under vigorous stirring at 70° C. for around 2 to 5 minutes. The yield point was measured as 54.85 Pa by means of a Rheolab MC100 (from Paar Physica) (cone angle 2°; truncation 0.05 mm; cone diameter 50 mm). The equipment's software contains a Casson evaluation method.

The emulsion was moderately stirred until the renewed gel formation beacame apparent. A hydrophobic (lipophilic) emulsifier was subsequently added to the secondary oil phase and the primary O/W phase dispersed in the secondary oil phase under moderate stirring for 2 to 5 minutes at room temperature. The emulsion had the following composition.

| | |
|---|---|
| Primary emulsion | |
| Water | q.s. |
| PEG-8 | 4.0 |
| Polyquaternium-31 | 0.5 |
| $C_{12}$–$C_{13}$ Alkyl Octanoate | 21.0 |
| Octyl Methoxycinnamate | 2.0 |
| Aminomethylpropanol (1%) | 1.0 |
| DMDM Hydantoin | 0.5 |
| Secondary oil phase | |
| Cyclomethicone | 19.5 |
| Cetyl Dimethicone | 1.5 |
| Cetyl Dimethicone Copolyol | 2.5 |

Spectroscopic measurement of the entrapment yield of the $O_1/W/O_2$ type multiple phase emulsion revealed 81%, and the droplets were easily recognizable in the emulsion. "q.s." means "quantum satis".

EXAMPLES 2 TO 5

Procedure as in example 1 but instead of $C_{12}$–$C_{13}$ Alkyl Octanoate in the primary emulsion the following were used: sesame oil (example 2), isopropyl palmitate (example 3), octyldodecyl myristate (example 4) and diisopropyl dimer dilinoleate (example 5). Almost identical values for the yield point and the yield as in example 1 were obtained.

EXAMPLES 6 AND 7

Production of an $O_1/W/O_2$ sun protection emulsion

In accordance with the basic method of example 1 two organic UV-B sun protection agents were additionally incorporated into the primary O/W-emulsion.

| | Example 6 | Example 7 |
|---|---|---|
| Primary emulsion | | |
| Water | q.s. | q.s. |
| Glycereth-26 | 4 | 4 |
| Acrylic acid/Acrylonitrogen copolymer | 0.5 | 0 |
| Polyquaternium-31 | 0 | 0.5 |
| $C_{12}$–$C_{13}$ Alkyl Octanoate | 12 | 12 |
| Tocopheryl Acetate | 1.0 | 1.0 |
| Octyl Methoxycinnamate | 7 | 7 |
| Benzophenone-3 | 3 | 2 |
| Amp95 Sol 1% | 0 | 2.0 |
| Amp95 Sol 10% | 2.0 | 0 |
| DMDN Hydantoin | 0.30 | 0.30 |
| Yield point (Pa) | 21.7 | 55.9 |
| Secondary oil phase | | |
| Cyclomethicone | 17.0 | 18.0 |
| Cetyl Dimethicone | 1.0 | 0.5 |
| Cetyl Dimethicone Copolyol | 2 | 3 |

The yield of the multiple phase emulsion of the $O_1/W/O_2$ type in example 7 was 88% and the appearance of the emulsion gel-like and very good. The emulsion of example 6 had a rather fluid consistence.

With a total of 10% the proportion of sun protection agents in the primary emulsion was very high and well above the hitherto known values.

The stability of the emulsion of example 7 was also very good and at temperatures of 4° C. as well as at 40° C. and 60° C. maintained a constant value for over 6 months.

The sun protection factor (SPF) of the emulsion of example 7 was 16 (standard deviation S.D.=2.81).

EXAMPLE 8 AND 9

Production of $O_1/W/O_2$ sun protection emulsions

In accordance with the basic method of examples 1 and 6 as well as 7 a third sun protection agent was additionally incorporated into the primary OW emulsion (example 8), or a mineral UV-absorbent into the secondary oil phase (example 9).

| | Example 8 | Example 9 |
|---|---|---|
| Primary emulsion | | |
| Water | q.s. | q.s. |
| Glycereth-26 | 4 | 4 |
| Polyquaternium-31 | 1.0 | 0.5 |
| $C_{12}$–$C_{13}$ Alkyl Octanoate | 10.0 | 12.0 |
| Tocopheryl Acetate | 1.0 | 0.5 |
| Octyl Methoxycinnamate | 7 | 7 |
| Benzophenone-3 | 3 | 3 |
| Butyl Methoxy-Dibenzoyl methane | 2.0 | 0 |
| Amp95 Sol. 1% | 1 | 1 |
| DMDM Hydantoin | 0 | 0.5 |
| Phenoxyethanol and PHB | 1.0 | 0 |
| Secondary oil phase | | |
| Cyclomethicone | 17.5 | 12 |
| Cetyl Dimethicone | 0.5 | 0.5 |
| 40% $TiO_2$ + $C_{12-15}$ Alcohol Benzoate | 0 | 5 |
| Cetyl Dimethicone Copolyol | 2 | 2.5 |

Both emulsions were obtained with a very good gel-like appearance, wherein the yield of multiple phase emulsion of example 8 was around 87%.

An SPF of 19 was measured for the emulsion of example 8 (SD=2.03) and for the emulsion of example 9 an SPF of 24.0 (SD=3.10).

The structure of the emulsion with the chemical sun protection agents in the primary oil phase and the physical UV-absorbent in the secondary oil phase was clearly verifiable under the microscope in polarized light. From microphotographs it can be seen how micronized $TiO_2$ is present as bright spots in the secondary phase and how the O/W-droplets contrast darkly, containing black oil droplets of the primary oil phase.

EXAMPLE 10 AND 11

$O_1/W/O_2$sun protection emulsion with active additives

In accordance with the basic method of example 1 further commonly used cosmetically active ingredients such as moisturizing agents, anti-inflammatory agents, wound-healing agents, radical scavengers, antioxidants as well as powdery products were added in the inner or outer phase in addition to the UV-filters.

| | example 10 | example 11 |
|---|---|---|
| Primary emulsion | | |
| Water | q.s. | q.s. |
| Glycereth-26 | 4 | 4 |
| Polyquaternium-31 | 0.5 | 0.5 |
| Glycerol | 7 | 0 |
| DL Panthenol | 2 | 0 |
| Allantoin | 0.5 | 0 |
| Amp.95 Sol. 1% | 1.0 | 1.0 |
| $C_{12}$–$C_{13}$ Alkyl Octanoate | 9.0 | 12.0 |
| Tocopheryl Acetate | 2 | 1.0 |
| Octyl Methoxycinnamate | 7 | 7 |
| Benzophenone-3 | 3 | 3 |
| Stearyl Glycerrhetinate | 0.5 | 0 |
| Tocopherol, Ascorbyl Palmitate, Ascorbic Acid and Citric Acid | 0.1 | 0 |
| Bisabolol | 0.5 | 0 |
| Fragance | 0.5 | 0 |
| DMDM Hydantoin | 0.3 | 0.3 |
| Yield point (Pa) | 47.7 | |
| Secondary oil phase | | |
| Cyclomethicone | 18.0 | 17 |
| Cetyl Dimethicone | 0.5 | 0.5 |
| Tospearl 145 | 0 | 1 |
| Cetyl Dimethicone Copolyol | 2 | 2 |

The multiple phase emulsion yield was 89%. Stable emulsions with good appearance were obtained in both cases.

EXAMPLE 12

$O_1/W/O_2$multiple phase emulsion as skin protection cream

In accordance with the basic method of example 1 skin-care and wrinkle-diminishing additives were added in place of UV-absorbents.

| | |
|---|---|
| Primary emulsion | |
| Water | q.s. |
| PEG-8 | 4 |
| Polyquaternium-31 | 0.5 |
| Glycerol | 5 |
| Amp.95 Sol. 1% | 1.0 |
| $C_{12}$–$C_{13}$ Alkyl Octanoate | 15.0 |
| Tocopheryl Acetate | 2 |
| Rhetinol Acetate 1 million U/g | 0.2 |
| Babassu oil | 3 |
| Octyl Methoxycinnamate | 2 |
| Bisabolol | 1.0 |
| DMDM Hydantoin | 0.3 |
| Secondary oil phase | |
| Cyclomethicone | 18.0 |
| Cetyl Dimethicone | 0.5 |
| Cetyl Dimethicone Copolyol | 2 |

EXAMPLE 13

$O_1/W/O_2$multiple phase emulsion with increased oil proportion

In accordance with the method of example 1 and the ingredients named therein the primary $O_1$/W-emulsion was formed with a 10% higher oil proportion. In spite of the increase in total oil phase volume, the consistency of the multiple emulsion remains high and comparable to example 1.

The emulsion showed good stability and good gel-like consistence and its characteristics corresponded approximately to those of example 1.

The reverse case, i.e. increase of the oil proportion of the outer oil phase, also resulted a stable multiple phase emulsion. In contrast with the increase in oil proportion in the inner oil phase however, the gel-like consistence was not so distinct. It is more interesting to add the oily excess in the primary $O_1$/W emulsion, so in the inner oil phase of the final multiple emulsion. By this way a more stable multiple emulsion with a gelled consistency was obtained.

COMPARATIVE EXAMPLE 1

A W/O emulsion was prepared according to the state of the art.

| | |
|---|---|
| Water | q.s. |
| sodium chloride | 0.5 |
| $C_{12}$–$C_{13}$ Alkyl Octanoate | 12.0 |
| Tocopheryl Acetate | 1 |
| Octyl Methoxycinnamate | 7 |
| Benzophenone-3 | 3 |
| DMDM Hydantoin | 0.3 |
| Cyclomethicone | 18.0 |
| Cetyl Dimethicone | 0.5 |
| Cetyl Dimethicone Copolyol | 2 |
| Total | 100 |

This conventional emulsion which has a composition very close to the formula of example 7 is very fluid. The water droplets were very small, however the stability was insufficient for cosmetic purposes. Phase separation took place after 3 months at room temperature and after 1 month at 40° C.

The emulsion had a very low viscosity of around 268 mPa·s and in comparison with the $O_1/W/O_2$ emulsion according to example 7 of the invention showed only a slight increase in the shear stress τ [Pa] with increasing shear rate [1/s] whereas this was the reverse in the emulsion according to example 7. A gel-like structure could therefore not be achieved with an emulsion of the above composition.

EXAMPLE 14

In accordance with the basic method of example 1 the silicone oil in the outer oil phase was replaced by an organic ester. Instead of Cetyl Dimethicone Dipolyol a different lipophilic emulsifier was used.

| | |
|---|---|
| Primary emulsion | |
| Water | q.s. |
| PEG-8 | 3 |
| Polyquaternium-31 | 0.5 |
| $C_{12}$–$C_{13}$ Alkyl Octanoate | 23.0 |
| Octyl Methoxycinnamate | 2.0 |
| Amp.95 Sol. 1% | 1.0 |
| DMDM Hydantoin | 0.5 |
| Multiple phase emulsion | |
| Hexyl Laurate | 13 |
| Sorbitan Oleate + | 2 |
| Polyglyceryl-3-Ricinoleate | |
| Total | 100 |

The lastingly stable O1/W/O2 emulsion shows that classical oils can also be used.

EXAMPLE 15

In accordance with the basic method of example 1 the viscoplastic primary emulsion $O_1/W$ was replaced by a different gelling agent, in this case with a smectite capable of water swelling. The smectite used was a synthetic Hectorite.

| | |
|---|---|
| Primary emulsion | |
| Water | q.s. |
| PEG-8 | 4.0 |
| Smectite (Hectorite) | 1.5 |
| Citric acid (20%) | 0.5 |
| Diisopropyl Dimer Dilinolate | 12 |
| hydrated Lecithin | 1.0 |
| Octyl Methoxycinnamate | 7 |
| Benzophenone-3 | 3 |
| DMDM Hydantoin | 0.5 |
| Multiple phase emulsion | |
| Cyclomethicone | 18.0 |
| Cetyl Dimethicone | 0.5 |
| Cetyl Dimethicone Copolyol | 2 |
| Total | 100 |

The primary emulsion had a yield point of 44.3 Pa and a plastic viscosity of only 0.0032 Pa·s. The droplet size was influenced by an emulsion modifier.

EXAMPLE 16

In accordance with the basic method of example 1 an emulsion according to the invention was prepared with additional color pigments in the outer phase. This emulsion is usable for make-up.

| | |
|---|---|
| Primary emulsion | |
| Water | q.s. |
| PEG-8 | 4.0 |
| Polyquaternium-31 | 0.4 |
| $C_{12}$–$C_{13}$ Alkyl Octanoate | 23.0 |
| Tocopheryl Acetate | 1.0 |
| Amp.95 Sol. 1% | 1.0 |
| DMDM Hydantoin | 0.5 |
| Multiple phase emulsion | |
| Isohexadecane | 2.5 |
| Covasil S white | 4.0 |
| Covasil S yellow | 2.0 |
| Covasil S red | 0.5 |
| Covasil S black | 0.5 |
| Neopentyl Glycol Diheptanoate | 7.0 |
| Sorbitan Oleate + | 2 |
| Polyglyceryl-3 Ricinoleate | |
| Total | 100 |

EXAMPLE 17

In accordance with the basic method of example 1 an emulsion according to the invention was prepared with additional micronized $TiO_2$ in the inner oily phase.

| | |
|---|---|
| Primary emulsion | |
| Water | q.s. |
| PEG-8 | 4.0 |
| Polyquaternium-3 | 0.5 |
| Aminomethylpropanol (Sol. 1%) | 1.0 |
| $C_{12}$–$C_{13}$ Alkyl Octanoate | 15.0 |
| Tocopheryl Acetate | 0.5 |
| Octalmethocycinnamate | 7.0 |
| Organic treated micronized $TiO_2$ | 5.0 |
| DMDM Hydantoin | 0.5 |

-continued

| Multiple phase emulsion | |
|---|---|
| Cyclomethicone | 17.5 |
| Cetyl Dimethicone | 0.5 |
| Cetyl Dimethicone Copolyol | 2.0 |
| Total | 100 |

What is claimed is:

1. Stable multiple phase $O_1/W/O_2$ emulsion comprising (a) a primary oil-in-water phase without emulsifier comprising a viscoplastic aqueous gel containing finely distributed oil droplets together with a gelling agent, wherein the thixotropic primary oil-in-water phase has a yield point in the range from 20 to 100 Pa, a plastic viscosity from 0.01 to 0.1 Pa·s and contains at least one lipophilic agent in the primary oil; and (b) a secondary oil phase in which the primary oil-in-water phase is present together with a lipophilic emulsifier; and wherein (c) the proportion of the inner oily phase is 10% to 35% by weight relative to the total weight of the emulsion.

2. Multiple phase emulsion according to claim 1, wherein the gelling agent is selected from the group consisting of a polyacrylate block copolymer and a smectite.

3. Multiple phase emulsion according to claim 1, wherein the primary oil includes an oil selected from the group consisting of linear organic esters, branched organic esters, polyunsaturated triglycerides, esters of hydroxy fatty acids and esters of glycols.

4. Multiple phase emulsion according to claim 1, wherein the primary oil-in-water phase for amplification of the viscoplastic characteristics additionally contains a substance selected from the group consisting of a Glycereth additive and a polyethylene glycol.

5. Multiple phase emulsion according to claim 1, wherein the inner or outer oil phase contains further actively effective lipophilic additives selected from the group consisting of UV-absorbents, vitamins, anti-inflammatory agents, polyunsaturated fatty acids, fatty acid esters, avocado oil, peanut oil, jojoba oil, and calendula oil; unsaponables selected from the group consisting of shea butter and avocado; lanolin; emollients selected from the group consisting of perhydrosqualene and perfluoro polyethers.

6. Multiple phase emulsion according to claim 1, wherein the aqueous phase additionally contains a hydrophilic agent selected from the group consisting of humectants, anti-inflammatory agents, peptides, proteins, water soluble vitamins and preservatives.

7. Multiple phase emulsion according to claim 1, wherein the secondary oil phase is an oil selected from the group consisting of silicone oil, synthetic fatty acid esters, paraffin oils and waxes.

8. Multiple phase emulsion according to claim 1, wherein the secondary oil phase further includes an emulsifier with an HLB value ≦8.

9. Multiple phase emulsion according to claim 1, wherein the secondary oil phase additionally comprises active agents selected from the group consisting of micronized inorganic absorbents, powdery products, Polyamid-12, polymethyl methacrylate and polymethyl silsesquioxane.

10. Multiple phase emulsion according to claim 1, wherein the proportion of the secondary oil phase is in the range from 15% to 30% by weight.

11. Multiple phase emulsion according to claim 1, wherein the primary oil phase contains an organic UV-absorbent and the secondary oil phase contains an inorganic mineral UV-absorbent.

12. Multiple phase emulsion according to claim 1, wherein the primary oil phase and the secondary oil phase together have a proportion by weight ≧50% relative to the total emulsion, and wherein the light oils are present in the secondary phase.

13. Multiple phase emulsion according to claim 1, wherein the inner oily phase contains a micronized mineral pigment selected from the group consisting of $TiO_2$, $SiO_2$, ZnO, and $ZrO_2$ in an amount of 0.5 g to 8% by weight.

14. Process for the production of a stable multiple phase $O_1/W/O_2$, emulsion, comprising the following steps:

dispersing a gelling agent in an aqueous phase until the formation of a gel;

heating the aqueous phase and a primary oil phase separately to a temperature up to 65° C.;

dispersing the primary oil phase in the aqueous phase by application of intensive shear stress at an increased temperature up to 70° C.;

cooling the primary O/W-emulsion subsequently under moderate stirring until gel formation occurs again;

dispersing the primary O/W-emulsion in the secondary oil phase at the surroundings temperature under moderate stirring.

15. A sun protection preparation comprising a stable multiple phase $O_1/W/O_2$ emulsion wherein the emulsion has a primary oil-in-water phase comprising a viscoplastic gel containing at least one organic UV-absorbent in the oil droplets, and a secondary oil phase formed by a silicone oil, said secondary oil phase containing one or more inorganic UV-absorbents, and wherein the proportion of the secondary oily phase is in the range from 15% to 30% by weight and wherein the proportion of the primary oily phase is in the range from 10% to 35% by weight, each relative to the total weight of the emulsion.

16. The sun protection preparation according to claim 15 comprising a make-up wherein the secondary oil phase contains additional color pigments.

* * * * *